United States Patent [19]

Iwase

[11] Patent Number: 5,067,838
[45] Date of Patent: Nov. 26, 1991

[54] VALVE UNIT FOR WRITING INSTRUMENTS OR LIQUID APPLICATORS

[75] Inventor: Yasuyuki Iwase, Fujioka, Japan

[73] Assignee: Mitsubishi Pencil Co., Ltd., Tokyo, Japan

[21] Appl. No.: 632,670

[22] Filed: Dec. 28, 1990

Related U.S. Application Data

[63] Continuation-in-part of Ser. No. 492,380, Mar. 12, 1990, abandoned, which is a continuation of Ser. No. 190,746, May 5, 1988, abandoned.

[30] Foreign Application Priority Data

May 8, 1987 [JP] Japan .................................. 62-69462

[51] Int. Cl.⁵ .......................... B43K 5/00; B43K 5/18; A46B 11/04
[52] U.S. Cl. ................... 401/206; 401/148; 401/273; 401/264; 401/180
[58] Field of Search ...................... 401/148–150, 401/178, 180, 182, 219, 220, 206, 264, 273, 272

[56] References Cited

U.S. PATENT DOCUMENTS

| | | | |
|---|---|---|---|
| 1,857,467 | 5/1932 | Marsh | 401/206 |
| 2,516,542 | 7/1950 | Blackman | 401/148 |
| 2,788,925 | 8/1954 | Ward | |
| 3,468,611 | 9/1969 | Ward | 401/206 X |
| 3,655,290 | 4/1972 | Griffith | 401/186 |
| 4,033,700 | 7/1977 | Spatz | 401/180 |
| 4,496,258 | 1/1985 | Tanaka et al. | 401/206 |
| 4,773,785 | 9/1988 | Katz | 401/272 X |

FOREIGN PATENT DOCUMENTS

| | | |
|---|---|---|
| 467107 | 2/1969 | Fed. Rep. of Germany . |
| 2517990 | 12/1982 | France . |
| 8605144 | 9/1986 | PCT Int'l Appl. ................. 401/206 |

Primary Examiner—Danton D. DeMille
Attorney, Agent, or Firm—Armstrong, Nikaido, Marmelstein, Kubovcik & Murray

[57] ABSTRACT

A valve unit for liquid applicators for applying liquid to articles, includes a spring support provided with a front and a rear openings, in an inner surface of which front opening is provided an annular projection serving as a sealing means; a valve seat provided with a cylindrical portion, and a seat portion; a valve stem provided with an edged piston portion brought into a slidable close contact with the cylindrical portion of the valve seat, the valve stem being seated on the valve seat at a front surface of the edged piston portion thereof; and a valve spring so resiliently urging the valve stem as to seat valve stem on the valve seat to close said valve unit.

2 Claims, 2 Drawing Sheets

VALVE UNIT FOR WRITING INSTRUMENTS OR LIQUID APPLICATORS

This application is a continuation-in-part of Ser. No. 492,380 filed Mar. 12, 1990, now abandoned, in turn, a continuation of Ser. No. 190,746, filed May 5, 1988, now abandoned.

BACKGROUND OF THE INVENTION

1. Field of the Invention

The present invention relates to a valve unit employed in writing instruments or liquid applicators suitable for applying liquid such as ink, cosmetic liquid, paint, liquid drug, adhesive and the like.

2. Description of the Prior Art

Hitherto, in this field of the art, there is no valve unit for feeding the liquid always at a constant rate to a liquid-application member of the writing instrument or liquid applicator when the valve unit is opened.

Consequently, in a conventional type of the writing instrument or liquid applicator, it is difficult to feed the liquid to the liquid-application member of the applicator at a constant rate without fail, because a so-called push-out operation of the writing instrument or liquid applicator for opening the valve unit substantially always varies in the length of its manual operation time to cause an excess or a shortage of the application liquid in the liquid-application member. The excess of the application liquid in the liquid-application member drops from the liquid-application member to smudge articles such as paper being coated with the application liquid. On the other hand, the shortage of the application liquid in the liquid-application member produces thin spots in writing or painting operation of the applicator. This is a problem inherent in the conventional writing instrument or liquid applicator.

SUMMARY OF THE INVENTION

It is an object of the present invention to provide a valve unit employed in a writing instrument or liquid applicator, which valve unit makes it possible to feed the application liquid to a liquid-application member at a constant rate each time the valve unit is opened so as to improve the writing or painting operation of the writing instrument of liquid applicator.

In the valve unit of the present invention, a valve stem of the valve unit is so moved that a predetermined amount of the application liquid is received in the interior of the liquid-application member, and then the thus received application liquid is supplied to the liquid-application member. Consequently, each time the valve unit is opened, the predetermined amount of the application liquid is metered and supplied to the liquid application member without any excess or shortage of the application liquid, whereby a uniform writing or painting operation can be conducted.

According to the present invention, there is provided:

A valve unit for writing instruments or liquid applicators for applying liquid to articles, comprising:

a spring support provided with a front and a rear openings, in an inner surface of which front opening is provided an annular projection serving as a sealing means;

a valve seat provided with a cylindrical portion, said valve seat being threadably connected with an inner surface of said rear opening of said spring support;

a valve stem provided with an edged piston portion brought into a slidable close contact with said cylindrical portion of said valve seat, said valve stem being seated on said valve seat at a front surface of said edged piston portion thereof, said edged piston portion constituting a radially outwardly extending annular flange, said valve stem being also provided with a slotted rear end portion to form a liquid-guide groove, in a position behind which slotted rear end portion a slidable shaft portion is so provided that an outer peripheral surface of said slidable shaft portion of said valve stem is brought into a slidable close contact with said annular projection of said spring support in a condition in which said valve stem is pushed forward; and a valve spring so resiliently urging said valve stem as to seat said valve stem on said valve seat to close said valve unit.

DESCRIPTION OF THE PREFERRED EMBODIMENTS

Figure 1:
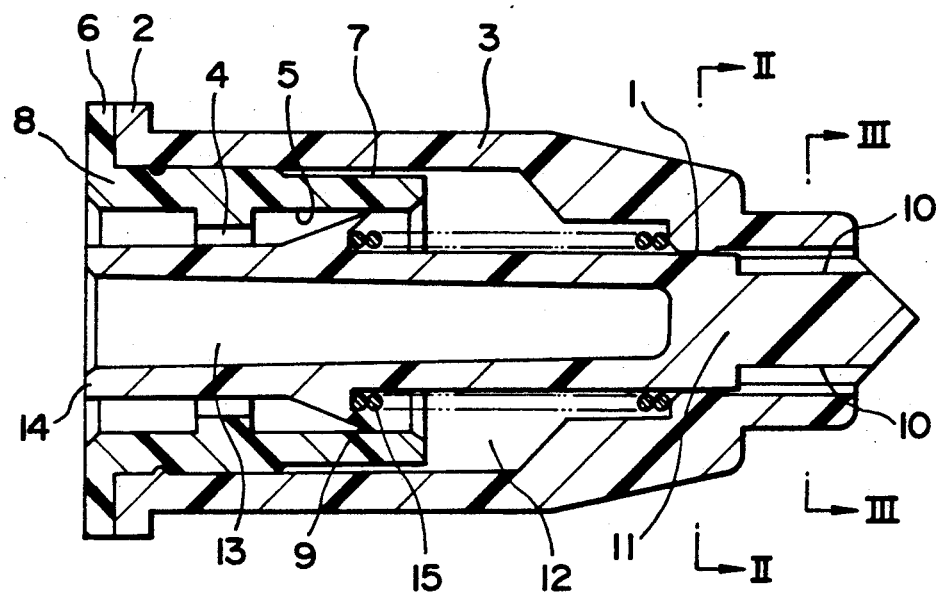
FIG. 1 is a longitudinal sectional view of a valve unit of the present invention, in a condition in which a predetermined amount of the application liquid is metered to the spring support of the valve unit.
Figure 2:
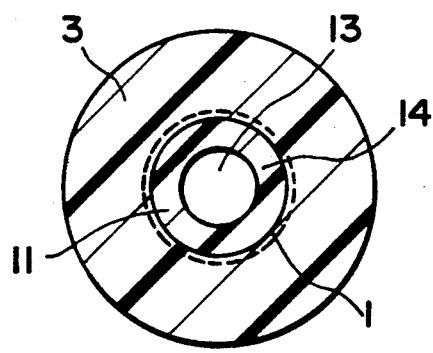
FIG. 2 is a cross-sectional view of the valve unit of the present invention shown in FIG. 1, taken along the line A—A of FIG. 1.
Figure 3:
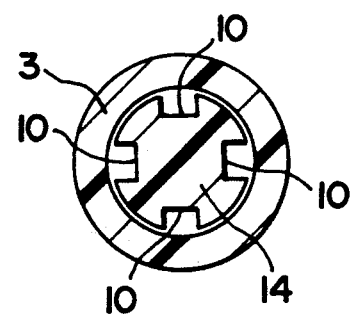
FIG. 3 is a cross-sectional view of the valve unit of the present invention shown in FIG. 1, taken along the line B—B of FIG. 1.

In the drawings: the reference numeral 3 denotes a spring support of a valve unit of the present invention; 14 a valve stem; and 8 a valve seat.

The spring support 3 is made of resilient plastics such as polyethylene and the like, and assumes a cylindrical shape. The spring support 3 is provided with a large-diameter opening in its front end, while provided with a small-diameter opening in its rear end. A sealing projection 1 is provided in an inner peripheral surface of the small-diameter opening of the spring support 3, which projection 1 assumes an annular-shaped flange with rounded edges. A radially outwardly projecting annular flange 2 is provided in an outer peripheral surface of a front end portion of the spring support 3.

The valve seat 8 is preferably made of the same material as that of the spring support 3. However, it is also possible that the valve seat 8 is made of any other suitable material. The valve seat 8 assumes a substantially cylindrical shape provided with a valve opening 4 in its central portion and a cylinder portion 5 in a position behind the valve opening 4. In outer diameter, the cylinder portion 5 of the valve seat 8 is slightly smaller than another cylinder portion following the cylinder portion 5. The valve seat 8 is provided with an annular flange 6 in its front end portion, and press-fitted to the large-diameter opening of the spring support 3 so that the flange 2 of the spring support 3 is brought into a close contact with the flange 6 of the valve seat 8.

A clearance 7 is provided between an outer surface of the cylinder portion 5 of the valve seat 8 and an inner surface of the spring support 3.

The valve stem 14 is also preferably made of the same material as that of the spring support 3. However, it is also possible that the valve stem 14 is made of any other suitable material.

The valve stem 14 is provided with an edged piston portion 9 which assumes a radially outwardly extending annular flange shape or skirt-like shape. An edged portion of the piston portion 9 is brought into a slidable close contact with the inner peripheral surface of the cylinder portion 5 of the valve seat 5 in a watertight manner.

A front surface of the edged piston portion 9 is tapered. The thus tapered front surface of the piston portion 9 of the valve stem 14 is seated on the valve seat 8 so that the valve opening 4 of the valve seat 8 is closed by the valve stem 14.

A rear end portion of the valve stem 14 is shaped into a conical form.

In the rear end portion of the valve stem 14 are provided four liquid-guide grooves 10 each of which has a predetermined axial length and is spaced apart from each other in parallel to each other. In front of the liquid-guide grooves 10, the valve stem 14 is provided with a shaft portion 11 which is brought into a slidable contact with the sealing projection 1 of the spring support 3, at which point a minor clearance (not shown) is left between annular sealing projection 1 and the outer surface of shaft portion 11, allowing a slight volume of liquid to pass therethrough.

Figure 4:
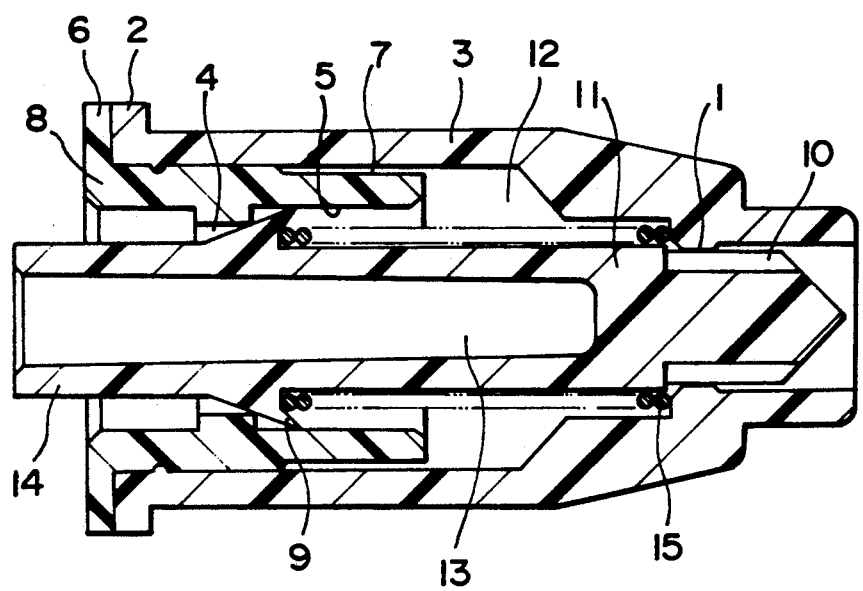
FIG. 4 is a longitudinal sectional view of the valve unit of the present invention, in a condition in which the valve unit is closed.

As shown in FIG. 4, the shaft portion 11 of the valve stem 14 is disengaged from the sealing projection 1 of the spring support 3 in a condition in which the edged piston portion 9 of the valve stem 14 abuts on the valve opening 4 of the valve seat 8. And, as shown in FIG. 1, when the edged piston portion 9 of the valve stem 14 is separated from the valve opening 4 of the valve seat 8, the shaft portion 11 of the valve stem 8 is again brought into a slidable close contact with the sealing projection 1 of the spring support 3 so that a predetermined amount of the application liquid is metered to the interior of the spring support 3.

An auxiliary reservoir 12 is defined by the interior hollow portions of the spring support 3 from the sealing projection 1 to the actual valve seat 8, and the exterior portions of the valve stem 14 from the exterior edged piston portion 9 to the exterior portion of the valve stem 14 which contacts the annular sealing projection 1 of the spring support 3.

The valve stem 8 is further provided with an axial bore 13 extending from a front end of the valve stem 8 to a portion in the vicinity of the rear end of the shaft portion 11 of the valve stem 8.

A valve spring 15 is mounted between a rear concave portion of the edged piston portion 9 of the valve stem 14 and an inner shoulder portion of the spring support 3 so as to resiliently press the tapered front surface of the edge piston portion 9 of the valve stem 14 against the valve opening 4 of the valve seat 8.

The valve unit of the present invention is fixedly mounted in the interior of a main body of the writing instrument or liquid applicator in which both of the flange 2 of the spring support 3 and the flange 6 of the valve seat 8 are clamped together in the main body of the writing instrument or liquid applicator. In the axial bore 13 of the valve stem 14 a rear end portion of a liquid-application member such as a pen core, brush and the like is inserted. In operation, the liquid-application member such as a pen core is subjected to the so-called push-out operation of the writing instrument or liquid applicator so that the valve stem 14 is axially moved.

The valve unit 6 of the present invention operates as follows:

In a condition in which no external force is applied to the valve stem 14, the valve stem 14 is resiliently urged forward under the influence of the valve spring 15 so that the valve opening 4 of the valve seat 8 is closed by the front tapered surface of the edged piston portion 9 of the valve stem 14, as shown in FIG. 4. The predetermined amount of the application liquid flows from a reservoir of the writing instrument or liquid applicator into the interior space 12 of the spring support 3 through the liquid-guide grooves 10 of the valve stem 14 so as to be metered thereto.

As shown in FIG. 1, when the valve stem 14 is pushed rearward against the resilient force of the valve spring 15 by a predetermined axial length, the interior space 12 of the spring support 3 is virtually sealed so that the predetermined amount of the application liquid is metered thereto. Then, when the valve stem 14 is further pushed rearward to separate the edged piston portion 9 of the valve stem 14 from the cylinder portion 5 of the valve seat 8, the predetermined amount of the application liquid is forced to pass through the valve opening 4 of the valve seat 8, whereby the predetermined amount of the application liquid is supplied to the liquid-application member of the writing instrument or liquid applicator. A small amount of application liquid escapes from chamber 12 through the minor clearance between shaft portion 11 and sealing projectional, allowing valve stem 14 to be pushed rearward. When the writing instrument or the liquid applicator is released from its push-out operation, the valve unit employed therein returns to its initial state shown in FIG. 4. As described above, in the writing instrument or liquid applicator, each time the push-out operation thereof is conducted to open the valve opening 4 of the valve seat 8, the predetermined amount of the application liquid is supplied to the liquid-application member of the writing instrument or liquid applicator.

In the above embodiment of the valve unit of the present invention, since the rear end portion of the valve stem 14 is shaped into the conical form, it is easy to insert the valve stem 14 into the rear end opening or small-diameter opening of the spring support 3. Further, since the front surface of the sealing projection 1 of the spring support 1 is tapered, it is easy to insert the shaft portion 11 of the valve stem 8 into an opening defined by the sealing projection 1 of the spring support 3. In addition, since the edged piston portion 9 of the valve stem 14 is shaped into the skirt-like form, the edged piston portion 9 is easily resiliently deformed to improve a slidable close contact with the cylinder portion 5 of the valve seat 8. In this case, since the clearance 7 is provided between the inner surface of the spring support 3 and the outer surface of the valve seat 8, there is no fear that the inner diameter of the spring support 3 varies even when the outer diameter of the cylinder portion 5 of the valve seat 8 is enlarged by the edged piston portion 9 of the valve stem 14. Consequently, it is possible to ensure the necessary sealing properties of the sealing projection 1 of the spring support 3.

What is claimed is:

1. A valve unit for liquid application instruments including writing pens which comprises:
   (a) a spring support provided with front and rear axial openings and having an annular projection to cooperatively serve as a virtual sealing means;

(b) an annular valve seat member affixed to said spring support and having an annular valve seat and an adjacent cylindrical portion on its inner periphery;

(c) a valve stem slidably mounted in said spring support and valve seat member with a valve body having a rearwardly facing outwardly directed skirt portion formed by a frusto-conical external surface to serve as a valve body while in contact with said annular valve seat, the free edge of said skirt being in sealing contact with said cylindrical portion; and (d) a coil spring interposed between said spring support and said valve stem urging said valve stem towards said valve seat.

2. A valve unit for liquid application instruments as described in claim 1, wherein an annular temporary reservoir is provided by said spring support, whereby predetermined amounts of liquids are measured into said annular temporary reservoir for application to a liquid applicator by said valve unit when said valve unit is closed.

* * * * *